United States Patent [19]
Stahl et al.

[11] Patent Number: 5,607,448
[45] Date of Patent: Mar. 4, 1997

[54] ROLLING TOURNIQUET

[75] Inventors: Daniel A. Stahl, 7081 Tyler St., Hollywood, Fla. 33024; Walter W. Johnson, Hollywood; Oscar Galvis, Hialeah, both of Fla.

[73] Assignee: Daniel A. Stahl, Hollywood, Fla.

[21] Appl. No.: 438,925

[22] Filed: May 10, 1995

[51] Int. Cl.⁶ .................................................. A61B 17/100
[52] U.S. Cl. ............................................ 606/203; 606/201
[58] Field of Search ...................................... 606/201, 202, 606/203; 601/148, 151; 24/93, 102 FC, 114.4, 163 K

[56] References Cited

U.S. PATENT DOCUMENTS

| | | | |
|---|---|---|---|
| 3,467 | 9/1969 | Cohen | 128/2.05 |
| 515,367 | 2/1894 | Rouseville . | |
| 832,352 | 10/1906 | Wallenthin . | |
| 1,757,060 | 5/1930 | Rieth . | |
| 2,068,173 | 1/1937 | Galves | 128/73 |
| 2,091,131 | 8/1937 | Cone | 128/57 |
| 2,258,720 | 10/1941 | Saighman | 606/203 |
| 2,333,237 | 11/1943 | Erekson | 128/327 |
| 2,461,201 | 2/1949 | Ellis | 2/311 |
| 2,511,269 | 6/1950 | Jones | 128/327 |
| 3,156,243 | 11/1964 | Sculley | 128/327 |
| 3,570,495 | 3/1971 | Wright | 128/327 |
| 3,586,001 | 6/1971 | Sanderson | 128/327 |
| 3,587,584 | 6/1971 | Keller | 128/327 |
| 3,654,931 | 4/1972 | Hazlewood | 128/327 |
| 3,814,085 | 6/1974 | Kupchinski | 128/57 |
| 4,066,084 | 1/1978 | Tillander | 128/327 |
| 4,228,792 | 10/1980 | Rhys-Davies | 128/24.3 |
| 4,566,436 | 1/1986 | Loefqvist | 128/1 R |
| 4,664,651 | 5/1987 | Weinshenker et al. | 604/115 |
| 4,848,324 | 7/1989 | Gavriely | 128/24 R |
| 5,304,202 | 4/1994 | Stahl | 606/203 |

FOREIGN PATENT DOCUMENTS 237486   7/1925   United Kingdom .

Primary Examiner—Michael Powell Buiz
Assistant Examiner—Mark S. Leonardo
Attorney, Agent, or Firm—Jacobson, Price, Holman & Stern PLLC

[57] ABSTRACT

A rolling tourniquet is provided including releasably connected ends. The tourniquet is longitudinally elastic, flexible and circular in cross section. Further, the tourniquet is highly resistant to radial deformation and the releasably connected ends include releasably joined end connecting members which may be quickly releasably jointed together against separation and quickly disconnected, when desired.

14 Claims, 3 Drawing Sheets

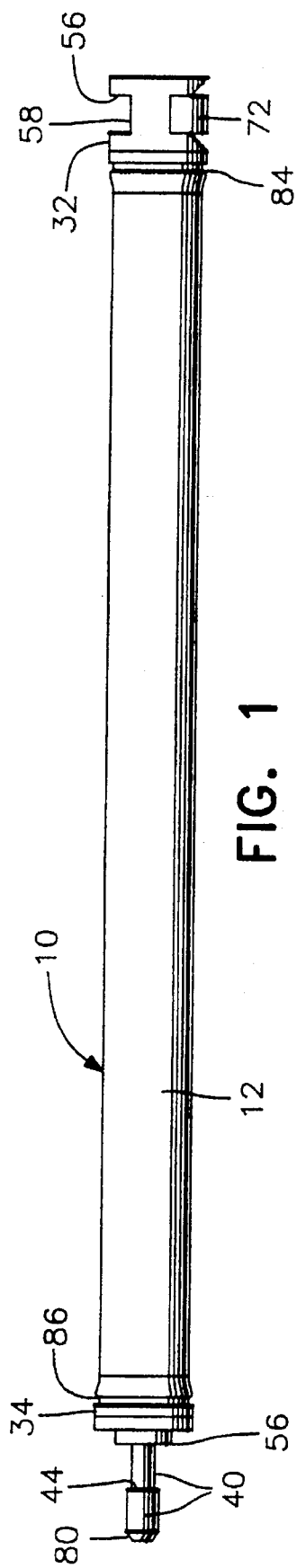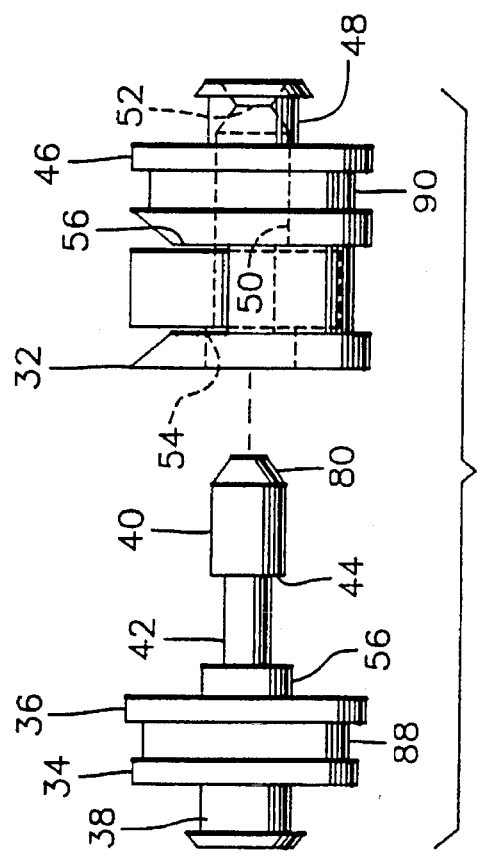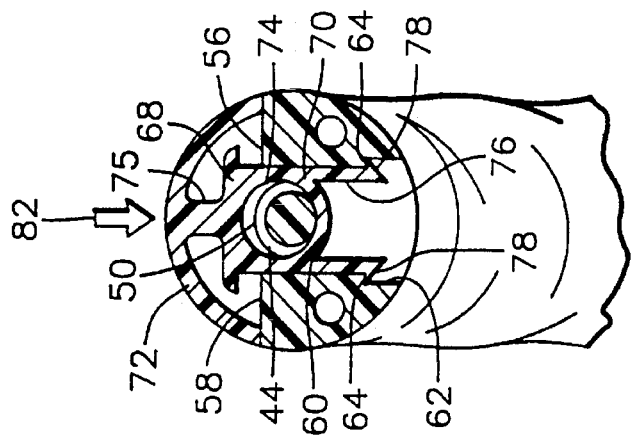

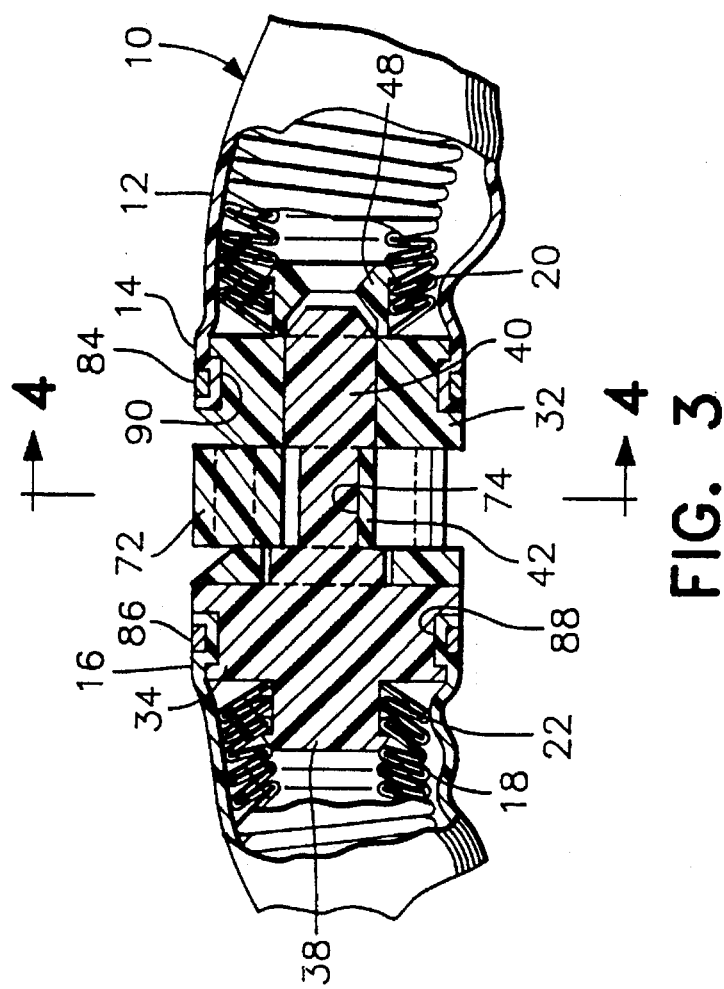
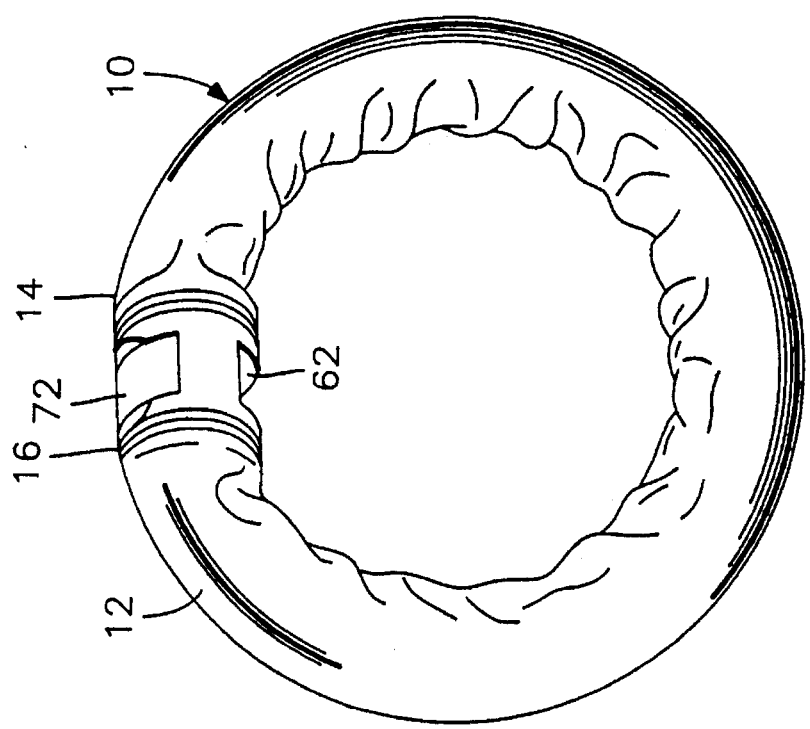

ROLLING TOURNIQUET

BACKGROUND OF THE INVENTION

1. Field of the Invention

This invention relates to an elongated, flexible and elastic member which may be curved into a generally annular shape with its opposite ends opposing each other and the opposite ends include coacting structure for removably joining the ends together in axial alignment with each other. The elastic member may be secured about a proximal portion of a body limb in longitudinally stretched condition such that it exerts a heavy generally radial inward force upon the limb throughout substantially the full length of a zone extending about the limb and with the inward pressure being applied throughout the zone being sufficient to locally compress not only veins closely beneath the skin surface but also sufficient to locally compress arteries of the limb further beneath the skin surface. The elongated member, once secured about a limb, then may be gradually rolled downwardly toward the distal end of the limb at a linear speed effective to "milk" both venous blood and arterial blood within the limb toward the distal end thereof, whereby to hyperextend at least one vein within the distal end portion of the limb.

2. Description of Related Art

While there have been many different forms of tourniquets heretofore utilized, such as those disclosed in U.S. Pat. Nos. 515,367, 832,352, 1,757,060, 2,068,173, 2,091,131, 2,258,720, 2,333,237, 2,461,201, 2,511,269, 3,156,243, 3,467,077, 3,570,495, 3,586,001, 3,587,584, 3,654,931, 3,814,085, 4,066,084, 4,228,792, 4,566,436, 4,664,651, 4,848,324 and United Kingdom Patent 237,486, dated July, 1925.

These prior patents, however, do not disclose structure operative, on a patient with substantial no cardiac output, to engorge a vein with blood so as to present a hyperextended vein into which a needle may be readily introduced for intravenous therapy.

In addition to the above prior patents, my prior U.S. Pat. No. 5,304,202 discloses fully the general structure and method accomplished by the instant invention and the disclosure of my prior U.S. Pat. No. 5,304,202 is incorporated herein by reference thereto.

The rolling tourniquet disclosed in U.S. Pat. No. 5,304, 202 includes connecting structure at the opposite ends of the elongated, flexible and elastic member thereof which enable the ends to be readily joined together and disengaged from each other. However, the instant invention incorporates two different forms of connecting structure which are more user friendly and also an improved form of elongated, elastic member which is self-reinforcing in order to prevent radial deformation thereof and which therefore is more efficient in applying more local heavy radial inward pressure upon an associated limb at least substantially the full length of an elongated zone extending completely about the limb.

BRIEF DESCRIPTION OF THE INVENTION

The rolling tourniquet of the instant invention includes a flexible, elastic outer tubular member which is telescoped over an inner core member of hollow, cylindrical configuration and which is corrugated throughout its length. The corrugated tubular core member is bendable to an extent that it may incorporate relatively short radius of curvature bends and a pair of end connecting members are provided and are each anchored relative to the corresponding ends of the outer tubular member and the inner corrugated tubular core member. The end connecting members are readily removably connectable to each other with the opposite ends of the inner and outer tubular members substantially axially aligned as a result of the rolling tourniquet being bent into a generally annular configuration.

When it is desired to use the rolling tourniquet for the purpose of hyperextending a vein adjacent the free end of a limb even though a patient has substantially no cardiac output, the tourniquet is applied about the proximal end of the patient's limb in a lengthwise stretched condition such that the tourniquet, when applied, delivers heavy radial inward pressure upon the proximal end of the limb throughout a narrow zone extending circumferentially about the limb. Thereafter, the tourniquet is slowly rolled downwardly along the limb toward the free end thereof independent of any sliding action of the tourniquet relative to the skin of the limb and at a linear speed effect to "milk" both venous blood and arterial blood within the limb proximal to the aforementioned zone toward the free end of the limb.

Of course, tourniquets for various size adults and for use on the arms and legs of adults will be provided in different sizes and also possibly different diameters. Further, circumferentially smaller and smaller diameter tourniquets will be provided for children while tourniquets to be used in conjunction with toddlers and babies will be even smaller in circumference and smaller in diameter.

The main object of this invention is to provide a rolling tourniquet of the type disclosed in my prior U.S. Pat. No. 5,304,202, but which will be of greater elasticity so as to be operative to apply a greater generally radial inward force on an associated limb, if desired.

Another object of this invention is to provide a rolling tourniquet in accordance with the preceding object and whose construction greatly resists radial compression or deformation of the tourniquet and thereby enables the zone of radial inward pressure applied by the tourniquet to the limb of a patient to be more narrow throughout its circumferential extent.

A further important object of this invention is to provide readily connectable and disconnectable end connecting members for the tourniquet to thereby facilitate use thereof even by relatively inexperienced persons.

Another very important object of this invention is to provide a rolling tourniquet with end connecting members which may be manufactured in small diameters and thereby enable the rolling tourniquet to be manufactured in diminutive sizes for use even on newborn babies.

A still further object of this invention is to provide a tourniquet which may be readily removed from a patient through the utilization of only one hand of a person attending the patient.

A final object of this invention to be specifically enumerated herein is to provide a tourniquet in accordance with the preceding objects and which will conform to conventional forms of manufacture, be of simple construction and easy to use so as to provide a device that will be economically feasible, long lasting and relatively trouble free in operation.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is an elevational view of the tourniquet in a straightened condition and with the ends thereof disengaged from each other.

FIG. 2 is a perspective view of the tourniquet with the ends thereof removably joined together and with the tourniquet in the form of an annulus.

FIG. 3 is an enlarged fragmentary sectional view illustrating the structure by which the end connectors of the tourniquet are removably joined together.

FIG. 4 is a vertical sectional view taken substantially upon the plane indicated by the section line 4—4 of FIG. 3.

FIG. 5 is an exploded elevational view of the end connecting members of the tourniquet.

DESCRIPTION OF THE PREFERRED EMBODIMENTS

Figure 6:
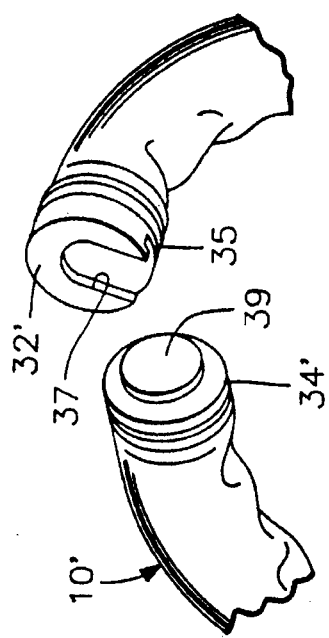
FIG. 6 is a fragmentary perspective view of the connected ends of a tourniquet constructed in accordance with the present invention and utilizing a modified form of end members.

Referring now more specifically to FIGS. 1–5, the rolling tourniquet is referred to in general by the reference numeral 10. The tourniquet 10 includes an outer elongated, flexible and elastic tubular member or tube 12 including opposite ends 14 and 16. In addition, the tourniquet 10 includes an inner circumferentially corrugated, tubular core member 18 including opposite ends 20 and 22 corresponding to the ends 14 and 16.

The tubular core member 18 is constructed of polyethylene and is marketed under the name "Extendoflex" by Cleveland Tubing. The corrugated tubular core member 18 is composed of interconnected and nested adjacent pairs of hollow frustoconial members 24 and 26. The outer peripheral portion of each member 26 is joined to the outer peripheral portion of an adjacent member 24 and the inner peripheral portion of each member 24 is joined to the inner peripheral portion of an adjacent member 26.

Thus it may be seen that the core member 18 comprises a corrugated member with longitudinally adjacent circumferential corrugations. When the corrugations of the core member 18 are closely adjacent each other as illustrated in the right and left hand portions of FIG. 8, a core member approximately ½ inch in diameter may be bent into an annulus as small as slightly greater than 5 inches in outside diameter before the outer peripheral portions of adjacent members 24 and 26 open as at 30 in FIG. 8. However, it is only at the outer periphery of the formed annulus that adjacent members 24 and 26 swing relative to each other to the open position at the 33 in FIG. 8, the inner peripheral portions of the formed annulus having the junctures between adjacent members 24 and 26 even more closely spaced together. Furthermore, because the corrugations are formed by adjacent nested members 24 and 26, the core member 28 strongly resists radial compression and deformity, especially at the inner periphery of the core member 18 when it is curved into a continuous annulus.

As may be noted from FIG. 2 of the drawings the outer tubular member 12 is loosely received over the core member 18 (unless otherwise desired) when the rolling tourniquet is in a non-longitudinally stretch condition. However, as the tourniquet 10 is longitudinally stretched, the effective diameter of the tubular member 12 is reduced and the inner surfaces of the tubular member 12 then contact the outer peripheries of the adjacent members 24 and 26 comprising the core member 18.

The tubular member 12 may be constructed of latex rubber tubing or any other suitable material and the ends of the rolling tourniquet are provided with end connecting members 32 an 34 which may be constructed of "Delrin".

The end connecting member 34 comprises a cylindrical body 36 including a coaxial flanged nipple 38 on one end and provided with a coaxial latch shaft 40 on its other end including a circumferential groove 42 defining an annular, radial shoulder 44.

The end connecting member 32 comprises a cylindrical body 46 including a coaxial flanged nipple 48 on one end and defining a central bore 50 therethrough including a first diametrically reduced portion 52 in the nipple 48 and a counterbore 54 at its end remote from the flanged nipple 48. The central bore 50 is slightly larger in diameter than the latch shaft 40 and the counterbore 54 is slightly larger than the diametrically enlarged base end 56 of the latch shaft 40. The body 46 further includes a notch 56 formed therein whose inner wall 58 extends along a major chord of the outer periphery of the body 46. Also, the body 46 includes a rectangular diametric passage 60 formed therethrough opening through the notch 56 at one end and through a diametrically enlarged passage end 62 at its other end, the diametrically enlarged passage end 62 defining opposite side shoulders 64.

A latch member 68 is provided and includes a slide portion 70 and an arcuate spring portion 72. The slide portion 70 is generally rectangular in cross section and is slidably receivable within the passage 60 from the end thereof opening into the notch 56. The slide portion 70 includes a central bore 74 formed therethrough which is registerable with the bore 50, an endwise outwardly projecting stem 75 on its end projecting into the notch 56 and from which the center portion of the spring portion 72 is supported and a pair of spring fingers 76 projecting outwardly of its other end and equipped with out turned barbs 78 received in the passage end 62 and abutted against the shoulders 64.

The spring portion 72 comprises a cylindrical segment whose outer surfaces are coextensive with the outer periphery of the body 46.

The free end of the latch shaft 40 is bevelled as at 80 and when the latch shaft 40 is displaced inwardly of the central bore 50, the bevelled portion 80 of the shaft 40 contacts the lower portion of the central bore 74 as illustrated in FIG. 2 and downwardly displaces the slide portion 70 to a position with the central bore 74 registered with the central bore 50, at which time the latch shaft 40 may be received through the central bore 74. During downward movement of the slide portion 70 in the passage 60, the free ends of the spring portion 72 (disposed in contact with the opposite ends of the inner wall 58) are flexed outward and as soon as the radial shoulder 44 of the latch shaft 40 passes through the central bore 74, the resiliency of the opposite ends of the spring portion 72 engaged with the inner wall 58 will return the slide portion 70 to the upper limit position thereof illustrated in FIG. 4 with the central bore 74 out of registry with the central bore 50. Thus, the radial shoulder 44 is engaged with the side of the slide portion 70 remote from the counter bore 52 to thereby lock the latch shaft 40 within the central bore 50.

Of course, when it is desired to remove the latch shaft 40 from the central bore 50, generally radial inward pressure is applied to the central portion of the spring portion 72 in a manner designated by the arrow 82 in FIG. 2, thus causing the slide portion 70 to again be displaced inwardly of the passage 60 until the central bore 74 registers with the central bore 50 thus allowing the shoulder 44 to be withdrawn through the central bore 74.

Figure 8:
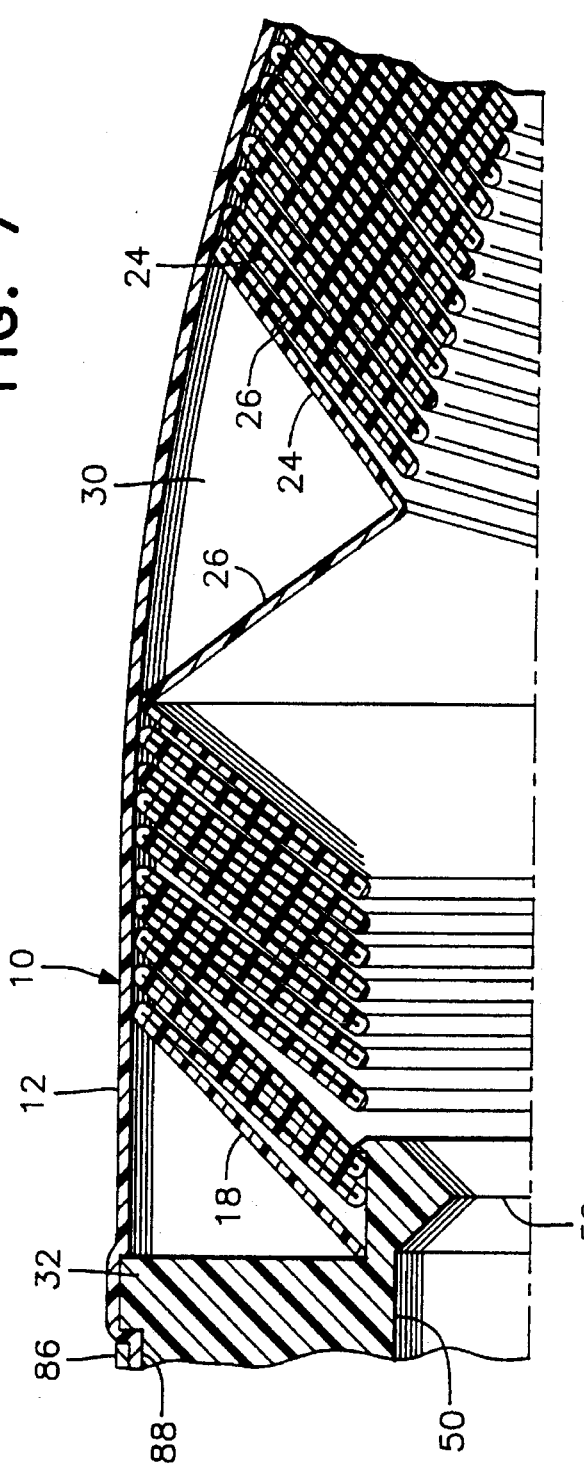
FIG. 8 is an enlarged longitudinal vertical sectional view of one end portion of the tourniquet illustrating the manner in which corresponding ends of the outer tubular member and inner corrugated tubular core member are joined to the corresponding end member and also the manner in which the corrugated tubular core member may be excessively curved while still enabling the inner periphery of the annular rolling tourniquet to strongly resist radial compression and/or deformation.

As may best be seen from FIG. 3 of the drawings and also from FIG. 8, one end of the core member 18 has three of the corrugations thereof snapped over the flanged nipple 38 and the other end of the core member 18 has three corrugations thereof snapped over the flanged nipple 48, thus securing opposite ends of the core member 18 to the connecting members 32 and 34. In addition, the tubular member 12 is loosely telescoped over the core member and has its opposite ends anchored relative to the connecting members 32 and 34 by bands 84 and 86 secured about the free ends of the tubular member 12 and tightly clamping the tubular member free ends within corresponding circumferential grooves 88 and 90 formed in the outer peripheries of the cylindrical bodies 36 and 46. Alternately, the tubing member ends may be secured to the connecting members 32 and 34 by adhesive.

As can be readily seen from FIGS. 1 and 3 of the drawings, the center area of the spring portion 72 of the latch member 68 may be readily inwardly displaced from the exterior of the connecting member 32.

Thus, the end connecting members 32 and 34 may be readily removably joined together merely by pushing the latch shaft 40 inwardly of the center 50 and the end connecting member 34 may be readily released from engagement with the end connecting member 32 merely by inwardly depressing the center area of the spring portion 72 and then axially displacing the end connecting members 32 and 34 apart.

Figure 7:
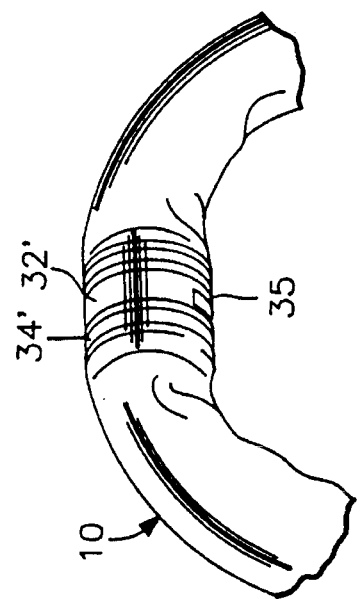
FIG. 7 is a perspective view of the ends of a tourniquet utilizing the modified form of end members and with the end members disconnected from each other.

With reference now more specifically to FIG. 7 of the drawings, there may be seen a pair of modified end connecting members 32' and 34'. The end connectors 32' and 34' are anchored relative to the core member 18 and the tubular member 12 in the same manner in which the end connecting members 32 and 34 are anchored thereto. However, the end connecting member 32' has a radial slot 35 formed therein adjacent its free end as well as a radial entrance slot 37. On the other hand, the end connecting member 34' includes an endwise outwardly projecting shank including a diametrically enlarged disc-shaped head 39 on its free end. The end connecting members 32' and 34' may be readily joined together merely by laterally displacing the head 39 inwardly of the slot 35 until the end connecting members 32' and 34' are axially aligned.

During usage, even though the tourniquet 10' illustrated in FIG. 7 may be rolled downwardly along an arm or a leg, it is been found that the end connecting members 32' and 34' will not accidentally disengage from each other. However, if desired, the opposite side walls of the slot 35 may be provided with slightly inwardly projecting detents (not shown) to engage behind the head 39 as the head 39 moves inwardly through the slot 35 to a point with the end connecting members 32' and 34' axially aligned with each other. Still further, the outer side of the head 39 could be provided with a center outwardly projecting detent which could seat within a central detent recess formed centrally in the end face of the end connecting member 32' opening axially through the slot 37. Also, the opposing side walls of the slot 35 could be slightly inwardly convergent at their outer ends and then curve away from each other to form a circular recess of slightly greater than 180° in angular extent to seatingly receive slightly more than one half of the disc-shaped head 39 therein. Of course, instead of including detents on the side walls of the slot 35, such detents could be provided on the side walls of the slot 37 for coaction with the shank from which the head 39 is supported and the side walls of the slot 37 could also be slightly convergent at their outer ends so as to snap engage the shank from which the head 39 is supported.

It is to be noted that larger size tourniquets, and particularly those used in the military, preferably will include the end connecting members 32 and 34. However, if the tourniquet is constructed of a size to be used on a small child or infant, the end connecting members 32' and 34' may advantageously be used, inasmuch as these end connecting members may be made considerably smaller in diameter than the end connecting members 32 and 34.

The foregoing is considered as illustrative only of the principles of the invention. Further, since numerous modifications and changes readily will occur to those skilled in the art, it is not desired to limit the invention to the exact construction and operation shown and described, and accordingly, all suitable modifications and equivalents may be resorted to, falling the scope of the invention.

What is claimed is as follows:

1. A limb encircling rolling tourniquet including an elongated, flexible outer elastic tube having first and second ends, an elongated, flexible and circumferentially corrugated substantially cylindrical inner tubular member, said tubular member being highly resistant to radial compression and at least somewhat longitudinally elastic, said tubular member including first and second ends and being telescoped within said tube with said tube first and second ends corresponding to said first and second ends of said tubular member, first and second end connecting members to which said first and second ends, respectively, of said tube and tubular member are anchored, said first and second connecting members including first and second connector structure, respectively, releasably engageable with each other releasably joining said connecting members together with said first and second ends of said tube and tubular member in substantially axially aligned relation, said tourniquet, when disposed about a body limb in a stretched condition with said connecting members releasably engaged with each other, being gradually rollable along said limb toward the free end thereof.

2. The rolling tourniquet of claim 1 wherein said first and second ends of said tube and tubular member are independently anchored to said first and second connecting members, respectively.

3. The rolling tourniquet of claim 1 wherein said corrugated tubular member is loosely telescoped within said tube when the latter is in a static, non-stretched condition, to thereby enable said tube to be at least initially longitudinally stretched before contracting radially into frictional contact with the radial outermost surfaces of said corrugated inner tubular member.

4. The tourniquet of claim 3 wherein said first and second ends of said tube and tubular member are independently anchored to said first and second connecting members, respectively.

5. The tourniquet of claim 1 wherein said corrugated tubular member is constructed of plastic material.

6. The tourniquet of claim 1 wherein said corrugated tubular member is constructed of hollow and nested flexive frustoconial wall sections with the small and large diameter ends of adjacent wall sections being integrally formed.

7. A limb encircling rolling tourniquet including an elongated, flexible outer elastic tube having first and second ends, an elongated, flexible substantially cylindrical inner tubular core member, said core member being longitudinally elastic, circumferentially corrugated and disposed within said elastic tube, said core member being highly resistant to radial compression and deformation, a pair of end connector members each having one pair of corresponding ends of said elastic tube and core member anchored thereto, said end connector members being readily releasably engageable with each other.

8. The tourniquet of claim 7 wherein said corresponding ends of said tube and core member each are independently anchored to the corresponding end connecting member.

9. The tourniquet of claim 7 wherein said first member includes an endwise outwardly projecting shaft thereon and said second end connecting member includes a cavity in which to releasably receive said shaft.

10. The tourniquet of claim 9 wherein said cavity comprises a longitudinal bore opening endwise outwardly of said second connecting member.

11. The tourniquet of claim 9 wherein said first and second connecting members include coacting latch structure readily releasably latching said shaft in said longitudinal bore against axial withdrawal therefrom.

12. The tourniquet of claim 9 wherein the outer end of said shaft includes an enlarged disc-shaped head, said cavity including a first laterally outwardly opening slot defined by said second connecting member and a second narrower entrance slot defined by said second connecting member opening into said first slot and through the end of said second connecting member, said shaft and head being receivable in said second and first slots, respectively.

13. A latch assembly including a substantially cylindrical first body member having an elongated latch shaft projecting lengthwise outwardly of one end of said first body member and a second substantially cylindrical body member defining a main bore opening endwise outwardly of one end of said second body member and into which said shaft is telescopically receivable, said shaft including an outer free end and a circumferential groove extending thereabout spaced from said outer free end defining a radial shoulder facing away from said outer end, said second body member including a transverse passage therein opening into said main bore, a latch member slidable in said passage between active and inactive positions, said latch member including a peripherally closed bore formed therethrough of a length slightly shorter than the axial extent of said groove, said latch member bore being precisely registered with and at least slightly out of registry with said main bore when said latch member is in said inactive and active positions, respectively, said latch member and second body member including coacting structure yieldingly biasing said latch member toward said active position.

14. A latch assembly including a substantially cylindrical first body member having an elongated latch shaft projecting lengthwise outwardly of one end of said first body member and a second substantially cylindrical body member defining a main bore opening endwise outwardly of one end of said second body member and into which said shaft is telescopically receivable, said shaft including an outer free end and a circumferential groove extending thereabout spaced from said outer free end defining a radial shoulder facing away from said outer end, said second body member including a transverse passage therein opening into said main bore, a latch member slidable in said passage between active and inactive positions, said latch member including a peripherally closed bore formed therethrough of a length slightly shorter than the axial extent of said groove, said latch member bore being precisely registered with and at least slightly out of registry with said main bore when said latch member is in said inactive and active positions, respectively, said latch member including a stem facing outwardly of said passage and terminating outwardly in a flexive cylindrical segment spring portion having outer surfaces coextensive with the outer periphery of said second body member when said latch member is in said active position, said passage opening outwardly into a notch formed in said second body member having an inner wall extending along a major chord of said second body member, said spring portion having its longitudinal mid-portion supported from said stem and including opposite end portions abutted against the opposite ends of said inner wall, said mid-portion, stem and latch member closed bore being inwardly displaceable in said passage to said inactive position causing yielding flexure of said end portions.

\* \* \* \* \*